United States Patent [19]
Rogers

[11] 4,359,477
[45] Nov. 16, 1982

[54] ENTEROCHELIN COMPLEXES

[75] Inventor: Henry J. Rogers, Clophill, England

[73] Assignee: National Research Development Corporation, London, England

[21] Appl. No.: 230,716

[22] Filed: Feb. 2, 1981

Related U.S. Application Data

[62] Division of Ser. No. 35,415, May 2, 1979, Pat. No. 4,269,850.

[30] Foreign Application Priority Data

May 5, 1978 [GB] United Kingdom ............... 18003/78

[51] Int. Cl.³ .................... A61K 31/28; C07F 5/00
[52] U.S. Cl. ................... 424/287; 260/429 J; 560/41; 562/448; 562/450; 424/309; 424/319
[58] Field of Search ............ 424/287; 260/429 J; 424/309, 319; 560/39, 41; 562/444, 448, 450

[56] References Cited

U.S. PATENT DOCUMENTS

| | | | |
|---|---|---|---|
| 2,538,792 | 1/1951 | Moersch | 560/39 |
| 4,182,754 | 1/1980 | Bonadio | 424/287 |

FOREIGN PATENT DOCUMENTS

| | | | |
|---|---|---|---|
| 1082872 | 1/1955 | France | 562/444 |

OTHER PUBLICATIONS

O'Brien et al., Biochimica et Biophysica Acta, 215(2), 1970, pp. 393-402.
Chem. Abstracts 83: 157095w.
Schlossberger et al., Z. Immun. Forsch., 107, pp. 215-217, (1950).
Rogers, H. J. et al., Biochemica et Biophysica Acta, 497(1977), pp. 548-557.

*Primary Examiner*—Ethel G. Love
*Attorney, Agent, or Firm*—Oblon, Fisher, Spivak, McClelland & Maier

[57] ABSTRACT

Complexes of enterochelin, and certain analogues thereof, with one of the metals indium and scandium are useful for the treatment of bacterial infections.

10 Claims, No Drawings

ENTEROCHELIN COMPLEXES

This is a divisional of application Ser. No. 35,415, filed May 2, 1979, now U.S. Pat. No. 4,269,850.

This invention relates to antibacterial agents.

The compound enterochelin is known to be an essential growth factor in relation to the virulence of a variety of bacteria, for example *Escherichia coli*, due, it is believed, to the ability of this substance to provide iron for the bacteria through competition with transferrin. It has now been found, however, that novel complexes of enterochelin with certain metals exert a quite considerable antibacterial action. The effect is very specific, being limited to a small group of metals only.

Accordingly the present invention comprises a complex of enterochelin, or an analogue thereof as defined below, with one of the metals indium and scandium.

Enterochelin is the cyclic trimer of 2,3-dihydroxybenzoyl-L-serine and has the structure

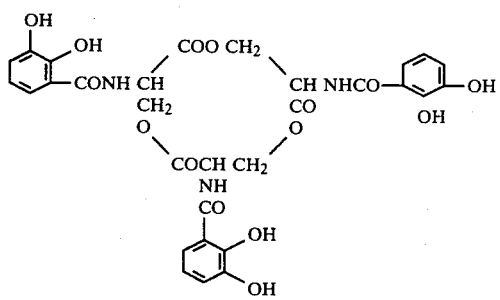

The present invention extends not only to complexes of the cyclic trimer but also to analogues thereof in which (a) the aliphatic ring system has been opened at one or more of the ester linkages to give a linear form of the trimer, or the corresponding dimer or monomer, in which one or both of the resulting free carboxy and hydroxy groups may optionally be in derivative form; and/or (b) the serine has instead the D-configuration.

Among the complexes of the linear compounds, it is generally the case that complexes of the trimer N,N',N''-tris(2,3-dihydroxybenzoyl)-O-seryl-O-serylserine are of more interest than complexes of the dimer N,N'-bis(2,3-dihydroxybenzoyl)-O-serylserine, which are in turn of more interest than those of the monomer N-(2,3-dihydroxybenzoyl)-serine. Such generalisations are also broadly applicable to complexes of the linear compounds in derivative form and when the serine is in the D- as well as when it is in the L-configuration, although the change from L- to D- configuration, for example in N-(2,3-dihydroxybenzoyl)-serine, may enhance the value of a compound. Derivatives of these linear compounds forming complexes according to the present invention include various common forms of derivative described in the art for carboxy and hydroxy groups, i.e. esters and salts such as those with the physiologically acceptable ions mentioned below, and also those derivatives in which dehydration has occurred at the aliphatic hydroxyl group to give a double bond, for example with the formation in the case of the linear trimer of the compound N,N',N''-tris(2,3-dihydroxybenzoyl)-O-(α-aminoacrylyl)-O-serylserine.

In the case of enterochelin itself, the metals in the form of their trivalent cation are combined with the six phenolic hydroxyl groups to give an octahedral complex. It is believed that this complex has a negative charge of three units due to the occurrence of the conversion $6OH \rightarrow 6O^-$ during the formation of the complex. It is preferred not to use the complex in its acidic form and conveniently, therefore, the net charge of the active anion is neutralised through the addition of a further cation or cations, for example three sodium ions or other ions suited to the context of antibacterial use of the complex, including particularly such additional physiologically acceptable ions as potassium, ammonium, etc. Such neutralisation may conveniently be effected, for example, by the use of aqueous sodium bicarbonate in formulating the complex. The complexes formed with analogues of enterochelin, as defined above, may also include additional ions which neutralise the net charge of the analogue-metal combination arising in a similar manner as just described and also in some cases from the presence of a carboxy group.

Enterochelin itself is most readily obtained by the microbiological process described in the art, whilst the linear analogues may also be obtained by such a process or a process involving the hydrolysis of enterochelin as described hereinafter, followed where applicable by appropriate derivitivisation. Analogues containing D-serine are prepared synthetically starting from 2,3-dihydroxybenzoyl-D-serine or a derivative thereof and, as appropriate, effecting extension to two or three such units, optionally followed by cyclisation, these steps involving manipulative procedures known in the art.

The complexes are conveniently prepared by the reaction in a suitable mutual solvent of enterochelin or its analogue and a salt of the appropriate metal which provides the metal ions. Salts of particular interest are those having a significant level of solubility in organic solvents in view of the relatively low solubility (ca 1 mM) of enterochelin in water, and for this reason the chlorides are preferred among halide salts. Suitable solvents for the reaction include mixtures of ketones and alcohols e.g. acetone/methanol and ketone alone. Aqueous alcohols may be used for the more water soluble linear analogues.

The reaction usually takes place quite rapidly at room temperature and, depending upon the particular reactants and the solvent used, precipitation may occur from the reaction solution or, alternatively, the solvent may be removed in vacuo to leave the complex. The complex may in either case, where desired, be washed with a suitable solvent, for example n-butanone followed by an ether such as diethyl ether, or alternatively some system such as n-butanone followed by n-butanone/glycerol which generally gives a material which is more readily dispersible in aqueous media.

Among the enterochelin complexes, scandium enterochelin is generally the most active but is also somewhat less tolerated than the only slightly less active inidium enterochelin. In the case of the complexes with analogues such as N,N'N''-tris (2,3-dihydroxybenzoyl)-O-(α-aminoacrylyl)-O-serylserine, however, the indium complex may show the higher activity. Where desired, mixtures of two or more complexes according to the invention may be employed, and other active substances may be incorporated into the composition, for example bacteriostatic substances such as kanamycin sulphate.

As indicated previously, the complex is conveniently formulated in a neutral form lacking an overall charge. The formulation of the complex for use as a pharmaceutical for both human and animal administration may be effected by a variety of methods, but usually involves the use of a physiologically acceptable diluent or carrier. The complex may, for instance, be applied as an aqueous suspension or emulsion for parenteral administration, the composition therefore preferably being sterile and pyrogen-free. The complex may also be compounded for oral administration in the presence of conventional solid carrier materials such as starch, lactose, dextrin and magnesium stearate. Alternative formulations are as aerosols, suppositories, cachets, and, for localised treatment, as suitable creams or drops.

The compositions may conveniently be formulated in unit dosage form, i.e. in the form of discrete portions each containing a unit dose, or a multiple or sub-multiple of a unit dose. Dosage levels may, however, vary quite considerably according to the particular type of treatment. The complexes are well tolerated so that, for example, mice will tolerate two doses per day each dose corresponding to 5.7 mg/Kg of scandium enterochelin, for a period of at least 5 days and often for about 11 days. In general, larger amounts are better tolerated as a series of spaced doses as compared with one single dose of the same amount, although single doses of the indium complex equivalent to 60 mg/Kg have been administered to mice without apparent adverse effect.

The compositions are of interest for the treatment of a range of bacterial infections, particularly those produced by gram negative bacteria and especially aerobic rather than anaerobic bacteria. Although such activity is not without certain exceptions, no activity having been observed against Pasteurella for example, it is nevertheless widespread, particularly among the Enterobacteriaceae. Thus activity has been observed against Escherichia, Pseudomonas and Klebsiella, Aerobacter and Salmonella for enterochelin complexes but those of linear analogues may be more restricted in activity. As well as showing activity against systemic infections enterochelin complexes do inhibit the growth of enteropathogenic *E. coli* in a medium containing the contents of the rabbit small intestine. An interesting feature of this activity is its enhancement by the presence of an iron chelator. The reason for this enhancement is believed to be that in contrast to the situation in serum, free iron is usually available in the gut, and removal of this free iron by an iron chelator enables the scandium or indium complex to function more efficiently in the treatment of infections in the gut by depletion of the supply of iron enterochelin competing for uptake. Conveniently, therefore, a composition according to the present invention may comprise an iron chelating agent in addition to the complex. A variety of physiologically acceptable iron chelating agents may be used and these may be of natural occurrence, for example rhodotorulic acid or particularly desferal, although synthetic agents not of natural occurrence are preferred, such as diethylenetriamine pentaacetic acid (DTPA) and particularly ethylene diamine tetraacetic acid (EDTA), and especially ethylenediamine di-(O-hydroxyphenyl) acetic acid (EDDA). Such compositions containing an iron chelating agent are of interest particularly in the treatment of gastroenteritis caused by *E. coli*, typhoid fever, cholera caused by *Vibrio cholerae* and dysentery caused by Shigella.

The invention is illustrated by the following Examples.

EXAMPLES

Example 1: Preparation of Scandium Enterochelin Complex

Equal volumes of 0.01 M enterochelin (prepared essentially according to the procedure of Rogers et al, Biochimica et Biophysica Acta, 1977, 497, 548) and 0.01 M scandium chloride ($ScCl_3.6H_2O$), both in n-butanone, are mixed at room temperature to give a white precipitate which is collected by centrifugation. The precipitate is washed [1] twice with n-butanone and then once with ether; removal of the residual ether giving the scandium enterochelin complex as an off-white powder which is relatively insoluble in both aqueous and organic solvents.

(1) In order to obtain a product suitable for injection, the above procedure is modified by the use of n-butanone (once) and then n-butanone saturated with glycerol (once) for washing the precipitate. The residual n-butanone is removed in vacuo to give the complex in a form which is readily dispersible in sterile saline containing 1% w/v sodium bicarbonate by means of sonication.

Example 2: Preparation of Indium Enterochelin Complex

Equal volumes of 0.01 M enterochelin and 0.01 M indium chloride ($InCl_3.3H_2O$), both in n-butanone, are mixed together and the solvent removed in vacuo to give the indium enterochelin complex. This is dispersible in saline containing 1% w/v sodium bicarbonate by means of sonication.

Example 3: Preparation of Complex of Indium with N,N',N''-Tris (2,3-Dihydroxybenzoyl)-O-(α-Aminoacrylyl)-O-Serylserine (A) Enterochelin (100 mg) is dissolved in 5.0 ml of acetone and the solution is added to 10 ml of water under nitrogen. Controlled alkaline hydrolysis is then carried out at pH 11.0 and 22° C. with the aid of a pH stat, the reaction being stopped by the careful addition of 1 N aqueous hydrochloric acid after 1.3 ester bonds have been hydrolysed. The resultant solution is evaporated to dryness in vacuo and the residue dissolved in 5.0 ml of water. After the addition of 0.10 ml of glacial acetic acid, the hydrolysate is fractionated by chromatography on a 3 cm×40 cm column of 625 Sephadex (superfine) using 6% v/v aqueous acetic acid to equilibrate and elute the column; the 2,3-dihydroxybenzoyl serine-containing compounds being detected by means of their adsorption at 300 nm. The slowest running component, which gives a single spot on paper chromatography, is isolated by extraction with ethyl acetate, washing, drying and evaporation to give a residue of N, N', N''-tris(2,3-dihydroxybenzoyl)-O-(α-aminoacrylyl)-O-serylserine [1].

(1) Other fractions contain N,N',N''-tris (2,3-dihydroxybenzoyl)-O-seryl-O-serylserine, N,N'-bis (2,3-dihydroxybenzoyl)-O-(α-aminoacrylyl)-serine, N,N'-bis(2,3-dihydroxybenzoyl)-O-serylserine, and N-(2,3-dihydroxybenzoyl)-serine and may be processed similarly to obtain these compounds. For example, the second fraction from the column [the first containing N-(2,3-dihydroxybenzoyl)-serine] contains N,N'-bis(2,3-dihydroxybenzoyl)-O-serylserine and this compound may be isolated by extraction with ethyl acetate, washing, drying and evaporation. The various compounds are readily identifiable through the description by O'Brien and Gibson in Biochimica et Biophysics Acta, 1970, 215, 393 of all of these compounds other than the dehydrated dimer. The procedure described by these authors provides an alternative route to four of the total of five compounds.

(B) A 0.2 mM solution of the indium N,N',N''-tris(2,3-dihydroxybenzoyl)-O-(α-aminoacrylyl)-O-serylserine complex [1] is prepared by mixing 0.10 ml of a solution of 2.36 mM of N,N',N''-tris (2,3-dihydroxybenzoyl)-O-(α-aminoacrylyl)-O-serylserine in ethanol with 0.049 ml of a solution of 5.0 mM In Cl$_3$·3H$_2$O in 0.1 N aqueous hydrochloric acid, and then adding 0.96 ml of water and sufficient solid sodium carbonate to raise the pH to 7.0.

(1) The scandium complex of this compound, and the scandium and indium complexes of the other compounds from the column are prepared analogously.

Example 4: In Vivo Tests of Bacteriostatic Activity of Scandium Enterochelin Complex Female TO mice weighing 23 to 25 grams are used in tests for antibacterial activity against three different types of bacteria, all injections of the scandium complex being given by the intraperitoneal route as a dispersion in sterile saline containing 1% w/v sodium bicarbonate.

(1) *Pseudomonas aeruginosa*

Twenty mice were each infected with $8.6 \times 10^4$ of a mouse-virulent strain (approximately 8000 LD$_{50}$). One half of the animals served as untreated controls whilst the other half received 0.2 ml of a 1.0 mM suspension of scandium enterochelin complex at intervals of 1,6,24,48,55,72 and 79 hours post-infection. The untreated controls had all died by 48 hours whilst the treated animals remained healthy and were finally killed 5 weeks later.

In a similar type of experiment where the animals were treated at intervals of 6,24,31,48 and 72 hours post-infection the survival rate was 30%.

(2) *Escherichia coli* 0141 K85

Forty mice received $9 \times 10^6$ *E. coli* 0141 (approx. 1 LD$_{100}$). One half of the group were given 0.2 ml 1.0 mM of scandium enterochelin complex at intervals of 1 and 6 hours post-infection. Ninety percent of the remaining untreated animals which served as controls had died by 32 hours. Eighty percent of the treated animals survived without ill effects and were killed one month later.

(3) *Klebsiella pneumoniae*

Twenty mice were infected with $8.4 \times 10^4$ bacteria (approx. 20 LD$_{50}$). Ten animals were treated with 0.2 ml 1.0 mM of scandium enterochelin complex at intervals of 6,24,31,48,55,72 and 79 hours post-infection and remained healthy during the course of the treatment. The ten untreated controls had died by the 5th day. The first death in the treated group did not occur until 8 days after infection. The survival rate of 20% was similar to that (40%) obtained when using kanamycin sulphate in the same treatment schedule.

Example 5: In Vitro Tests of Bacteriostatic Activity of Indium and Scandium Enterochelin Complexes Against *E. coli* Serotypes Associated with Gastroenteritis Two alternative forms of medium are used. The fist medium (RIF) consists of chyme from the rabbit small intestine mixed with medium 199 and 6% w/v aqueous NaHCO$_3$, and then diluted with saline, the proportions being such as to give a final medium containing 10% v/v chyme, 0.2% w/v NaHCO$_3$ and of one quarter strength in medium 199, having a pH of 7.5. The second medium (TSB) which acts as a control is trypticase soy broth containing 0.6% w/v NaHCO$_3$. Each medium is stirred at 37° C. under an atmosphere of 5% CO$_2$, 85% N$_2$ and 10% O$_2$ (by volume). The media are inoculated with *E. coli* of serotype 0111, 0141 or 0149 using in each case an inoculum of ca. 10$^3$ bacteria per ml. In certain cases one of the iron chelators ethylenediamine di-(O-hydroxyphenyl) acetic acid (EDDA), diethylenetriaminepentaacetic acid (DTPA), ethylenediaminetetra acetic acid (EDTA) and desferal (DF) is added prior to inoculation. In certain cases 10μM of the In$^{3+}$ or Sc$^{3+}$ complex of enterochelin is added 2 hours after inoculation. The levels of *E. coli* population in the various medium samples are determined at intervals by viable counts of dilutions on plates. The values of log$_{10}$ of viable counts at 7 hours after inoculation are shown in Table 1 below.

TABLE 1

| E. coli serotype | Medium | Iron Chelator | Enterochelin complex | log 10 viable count at 7 hours |
|---|---|---|---|---|
| 0111 | RIF | — | Sc | 7.2 |
| 0111 | RIF | EDDA | Sc | 4.7 |
| 0141 | RIF | EDDA | — | 8.2 |
| 0141 | RIF | EDDA | Sc | 5.0 |
| 0149 | RIF | EDDA | — | 8.6 |
| 0149 | RIF | EDDA | Sc | 5.3 |
| 0141 | RIF | DTPA | — | 8.7 |
| 0141 | RIF | DTPA | In | 7.0 |
| 0141 | RIF | EDTA | — | 8.7 |
| 0141 | RIF | EDTA | In | 6.6 |
| 0141 | RIF | EDDA | — | 8.5 |
| 0141 | RIF | — | In | 8.5 |
| 0141 | RIF | EDDA | In | 5.5 |
| 0141 | TSB | DF | — | 8.5 |
| 0141 | TSB | — | In | 7.9 |
| 0141 | TSB | DF | In | 5.8 |
| 0141 | TSB | DF | Sc | 5.4 |

Example 6: In Vitro Tests of Bacteriostatic Activity of Complex of Indium with N,N',N"-Tris(2,3-Dihydroxybenzoyl)-O-(α-Aminoacrylyl)-O-Serylserine Rabbit plasma is inactivated by heating at 56° C. for 30 minutes and then inoculated with *Escherichia coli* 0141 at 37° C. under an atmosphere of 5% CO$_2$; 85% N$_2$ and 10% O$_2$ (by volume). After 2 hours the indium N,N',N"-tris(2,3-dihydroxybenzoyl)-O-(α-aminoacrylyl)-O-serylserine complex is added to a final concentration of 2 μM to one set of plasma samples whilst a second set remains untreated as a control. The level of *E. coli* population in the plasma samples are determined at inoculation and at 2,4,6 and 7 hourly intervals thereafter for both sets by viable counts of dilutions on plates. The values of log$_{10}$ of viable counts are shown in Table 2 below.

TABLE 2

| | log 10 Viable Counts | |
|---|---|---|
| Time (hours) | Control | 2 M In$^{3+}$ complex |
| 0 | 2.71 | 2.71 |
| 2 | 3.91 | 3.90 |
| 4 | 4.63 | 4.20 |
| 6 | 5.74 | 4.52 |
| 7 | 6.38 | 4.53 |

A similar in vitro experiment has shown activity for the indium complex of N,N'-bis(2,3-dihydroxybenzoyl)-O-serylserine against Klebsiella.

I claim:

1. An indium or scandium complex of a compound containing at least one serine moiety in its D- or L-configuration and selected from the group consisting of N,N',N"-tris (2,3-dihydroxybenzoyl)-O-seryl-O-serylserine, N,N'-bis (2,3-dihydroxybenzoyl)-O-serylserine, and derivatives of said compound involving the carboxy and hydroxyl groups of said compound, the derivatives of said carboxy group being pharmaceutically acceptable esters and salts thereof and the derivatives of said hydroxyl group being the resultant double bond from the dehydration of said compound involving said hydroxyl group.

2. The complex of claim 1, wherein said complex is the indium complex.

3. An antibacterial pharmaceutical composition, comprising:

an antibacterially effective amount of a complex of a compound containing at least one serine moiety in its D- or L- configuration and selected from the group consisting of N,N′,N″-tris (2,3-dihydroxybenzoyl)-O-seryl-O-serylserine, N,N′-bis(2,3-dihydroxybenzoyl)-O-serylserine and derivatives of said compound involving the carboxy and hydroxyl groups of said compound, the derivatives of said carboxy group being pharmaceutically acceptable esters and salts thereof and the derivative of said hydroxyl group being the resultant double bond from the dehydration of said compound involving said hydroxyl group, with indium or scandium.

4. The composition of claim 3, wherein said complex is the indium complex.

5. A method of treating bacterial infections in a human or animal subject, comprising:

administering to said subject an antibacterially effective amount of a complex of a compound containing at least one serine moiety in its D- or L- configuration and selected from the group consisting of N,N′,N″-tris(2,3-dihydroxybenzoyl)-O-seryl-O-serylserine, N,N′-bis (2,3-dihydroxybenzoyl)-O-serylserine and derivatives of said compound involving the carboxy and hydroxyl groups of said compound, the derivatives of said carboxy group being pharmaceutically acceptable esters and salts thereof and the derivative of said hydroxyl group being the resultant double bond from the dehydration of said compound involving said hydroxyl group, with indium or scandium.

6. The method of claim 5, wherein said complex is the indium complex.

7. The composition of claim 3, which additionally comprises a physiologically acceptable iron chelating agent.

8. The composition of claim 7, wherein said agent is not one of natural occurrence.

9. The composition of claim 8, wherein said agent is diethylene triamine pentaacetic acid, ethylene diamine tetraacetic acid or ethylene diamine di-(O-hydroxyphenyl) acetic acid.

10. The composition of claim 9, wherein the agent is ethylene diamine di-(O-hydroxyphenyl) acetic acid.

* * * * *